United States Patent [19]
Swinson et al.

[11] Patent Number: 6,110,506
[45] Date of Patent: *Aug. 29, 2000

[54] DASC COMPOSITIONS, PROCESS FOR PREPARING SAME AND SUSPENSIONS CONTAINING SAME

[75] Inventors: Joel Swinson, Ooltewah; Richard D. Giles, Signal Mountain; Jack Pitkin; Glenda Fleming, both of Chattanooga, all of Tenn.; David B. Blum, Wayne, N.J.

[73] Assignee: Chattem Chemicals, Inc., Chattanooga, Tenn.

[*] Notice: This patent is subject to a terminal disclaimer.

[21] Appl. No.: 09/475,620

[22] Filed: Dec. 30, 1999

Related U.S. Application Data

[63] Continuation of application No. 08/824,509, Mar. 26, 1997.

[51] Int. Cl.[7] .............................. A61K 9/10; A61K 33/10; C01B 31/30; A01N 59/06; A01N 25/04

[52] U.S. Cl. ........................ 424/686; 424/489; 424/490; 424/715; 514/819; 514/820; 514/925; 514/926; 514/927; 514/928; 514/937; 514/951; 514/952

[58] Field of Search ...................... 424/686, 489, 424/490, 715; 514/819, 820, 925, 926, 927, 928, 937, 951, 952; 556/175, 182, 183, 184, 185; 423/420.2

[56] References Cited

U.S. PATENT DOCUMENTS

| | | | |
|---|---|---|---|
| 2,783,179 | 2/1957 | Grote | 424/686 |
| 2,999,790 | 9/1961 | Alford | 424/689 |
| 3,272,704 | 9/1966 | Beekman | 424/683 |
| 3,591,680 | 7/1971 | Greene et al. | 424/601 |
| 3,629,229 | 12/1971 | Schmank | 536/121 |
| 3,911,090 | 10/1975 | Hem et al. | 423/419.1 |
| 4,112,072 | 9/1978 | Rubino et al. | 424/683 |
| 4,115,553 | 9/1978 | Rubino et al. | 424/683 |
| 4,676,984 | 6/1987 | Wu et al. | 424/689 |
| 5,874,112 | 2/1999 | McNally et al. | 424/690 |
| 5,914,135 | 6/1999 | Dubek et al. | 424/687 |

FOREIGN PATENT DOCUMENTS 275834  7/1988  European Pat. Off. .

OTHER PUBLICATIONS

Shad, D.N. et al., "Mechanism of interaction between polyols and aluminum hydroxide gel," Journal of Pharmaceutical Sciences, vol. 70(10), pp. 1101–1104, Oct. 1981.

*Primary Examiner*—John Pak
*Attorney, Agent, or Firm*—Amster, Rothstein & Ebenstein

[57] ABSTRACT

The present invention provides DASC compositions, which upon introduction into aqueous solutions, form stable, non-gritty suspensions. The present invention also provides stable, non-gritty suspensions comprising the DASC compositions of the present invention admixed in aqueous solutions. In addition, the present invention provides processes for preparing the suspensions which comprise admixing the DASC compositions of the present invention with aqueous solutions. Finally, the present invention provides processes for preparing the DASC compositions of the present invention.

17 Claims, No Drawings

DASC COMPOSITIONS, PROCESS FOR PREPARING SAME AND SUSPENSIONS CONTAINING SAME

This is a continuation of application Ser. No. 08/824,509, filed Mar. 26, 1997, the contents of which is hereby incorporated by reference in its entirety.

FIELD OF THE INVENTION

The present invention is directed to improved dihydroxy aluminum sodium carbonate (DASC) compositions, which unlike prior art DASC, form stable, non-gritty suspensions in aqueous solutions. The improved properties of the DASC compositions of the present invention render the compositions particularly useful as components of liquid antacids, and other consumer and industrial products, for which stable, non-gritty suspensions are desirable.

BACKGROUND OF THE INVENTION

DASC is a known aluminum salt which exhibits excellent acid neutralizing capacity, and therefore is particularly useful in antacid formulations. (See, Grote, U.S. Pat. No. 2,783,179, issued Feb. 26, 1957). However, the use of prior art DASC as the active ingredient in antacid formulations has been generally limited to non-liquid formulations (e.g. Rolaid tablets) because prior art DASC does not form stable aqueous suspensions at concentrations that produce acceptable acid neutralizing capacity. In addition, even dilute suspensions of prior art DASC possess an undesirable gritty appearance and taste, and rapidly form a sediment layer.

Several attempts have been made to stabilize aluminum hydroxide suspensions. For example, Alford, U.S. Pat. No. 2,999,790, issued Sep. 12, 1961, described combining hexitols such as sorbitol and mannitol with aluminum hydroxide gels in water to prevent thickening and hardening of the aluminum hydroxide gels.

Greene, et al., U.S. Pat. No. 3,591,680, issued Jul. 6, 1971, described the use of hydroxypropyl cellulose for stabilizing antacids such as magnesium carbonate, magnesium hydroxide, aluminum hydroxide, or calcium carbonate, which essentially involved slurrying the dry actives with water and hydroxypropyl cellulose.

Schmank, U.S. Pat. No. 3,629,229, issued Dec. 21, 1971, described water soluble antacid formulations that were prepared by reacting aluminum powder or aluminum isopropoxide with polyhydroxyl hydrocarbons.

Rubino, et al., U.S. Pat. No. 4,112,072, issued Sep. 5, 1978, described antacid compositions that were prepared by codrying hydrous, gelatinous aluminum-hydroxide materials with di- or trihydroxy alcohols.

Beekman, U.S. Pat. No. 3,272,704, issued Sep. 13, 1966, described antacid compositions that were prepared by co-drying aluminum hydroxide and magnesium hydroxide gels with hexitols.

Hem, et al., U.S. Pat. No. 3,911,090, issued Oct. 7, 1995, described antacid compositions containing silicate anions and aluminum hydroxy carbonates which purportedly possess the antacid properties of liquid aluminum hydroxide gels.

However, prior to the present invention, no methods have been taught or suggested for preparing DASC compositions which, upon introduction into aqueous solutions, results in suspensions that have the desired properties of stability and non-grittiness.

SUMMARY OF THE INVENTION

The present invention is based upon the discovery by the inventors of DASC compositions, which unlike prior art DASC, form stable, non-gritty suspensions in aqueous solutions. The DASC compositions of the present invention, unlike prior art DASC, also can be formulated so that upon introduction into aqueous solutions, the resulting suspensions not only possess the aforementioned desired physical properties, but also have acceptable acid neutralizing capacities. Accordingly, the DASC compositions of the present invention are particularly desirable for use in liquid antacid formulations.

In addition to stability and non-grittiness, the DASC compositions of the present invention also can be formulated to have gelling and/or translucent properties. Accordingly, the DASC compositions of the present invention are also suitable for use as components of other consumer or industrial products such as tooth pastes, soaps, detergents, pharmaceuticals, lotions, nutriceuticals, plastic additives, chemical foaming agents, acid scavengers, gellants, cleaners, and the like, for which stable and non-gritty, and/or gelling and/or translucent properties are desirable.

The properties of the DASC compositions of the present invention relate to the manner in which the compositions are prepared. Specifically, it has been found that if DASC is synthesized under certain temperature conditions, then the resulting dried DASC composition, when reconstituted in an aqueous solution, results in a suspension having the desired properties. It also has been found that if at least one polyol is included in freshly synthesized DASC before drying, or is included during the reaction of DASC, then the resulting co-dried DASC/polyol composition, when reconstituted in an aqueous solution, will also result in a suspension that possesses the desired properties of stability and non-grittiness. In addition, depending upon the choice of polyol, the suspensions also may be prepared to be translucent and/or gelling. Accordingly, in addition to the improved DASC compositions and suspensions containing the same, the present invention also provides processes for preparing the DASC compositions of the present invention.

Additional objects of the invention will be apparent from the description which follows.

DETAILED DESCRIPTION OF THE INVENTION

The composition of the present invention is directed to a powder that comprises DASC, which upon introduction into an aqueous solution, forms a stable, non-gritty suspension. As used herein, "stable" means that the powder does not settle or separate in the suspension but rather stays in solution resulting in a suspension having a homogeneous appearance. This stability lasts for at least three months, preferably at least six months, and most preferably for up to a year or more. "Non-gritty" means that the suspension has only minor or no grittiness.

The powder of the present invention also can include at least one polyol. Suitable polyols include but are not limited to sorbitol, glycerin, mannitol, maltodextrin, pentaerythritol, fructose, glucose and sucralose. However, as discussed in the Examples below, the inventors of the present invention have found that polyols such as propylene glycol, 1,3-butylene glycol, neopentyl glycol, polyethylene glycol and sodium carboxymethylcellulose do not result in suspensions having the desired stability and non-gritty properties. Accordingly, such polyols are not included within the term "polyols" as used herein. The ratio of DASC:polyol to arrive at the desired properties may vary. However, in the preferred embodiment, the weight ratio of DASC:polyol is 0.67:1 to 19:1 (40–95% DASC), and more preferably is 1.5:1 to 5:1 (60–83% DASC).

The DASC powder of the present invention is prepared by reacting an organoaluminum compound with a carbonate in an aqueous solution at a temperature of between about −20° C. and about 10° C. The molar ratio of organoaluminum compound:carbonate is preferably 1:1 to 1:3. Sodium chloride or isopropyl alcohol also may be added to the reaction mixture. Suitable organoaluminum compounds include aluminum alkoxides such as aluminum iso-propoxide, aluminum ethoxide and aluminum sec-butoxide. Preferably, the organoaluminum compound is aluminum iso-propoxide. The inventors of the present invention have found that the use of aluminum chloride or sodium aluminate does not result in a suspension having the desired properties. Accordingly, aluminum chloride and sodium aluminate are not included within the term "organoaluminum compound" as used herein. The carbonate includes but is not limited to sodium bicarbonate and sodium carbonate, but is preferably sodium bicarbonate.

After the DASC is prepared using the above process, it is isolated by methods known in the art such as filtration, centrifugation, settling, decanting or a combination thereof. For batch preparations, filtration is preferred. The DASC may then be washed with water following isolation to remove isopropyl alcohol formed during the reaction. The isolated DASC is then dried into powder form by suitable methods including but not limited to air-drying, oven-drying, fan-drying, spray-drying or a combination thereof.

When at least one polyol is included in the powder with DASC, it has been found that the desired DASC/polyol powder can be prepared by certain modifications to the above process. Specifically, the polyol(s) can be added directly to the freshly prepared wet DASC before or after the isolation step, or can be combined with the organoaluminum compound and the carbonate reactants before DASC is formed. However, it is preferred that the polyol is added after DASC has been isolated since it has been found that when the polyol is combined with DASC or the reactants before isolation of DASC, some of the polyol may be lost in the isolation step. The inventors also have found that dry DASC cannot be combined with the polyol in water and result in an aqueous DASC/polyol suspension having the desired properties. Accordingly, the use of previously prepared dry DASC is not encompassed by the processes of the present invention.

The organoaluminum compound and carbonate used in preparing the DASC/polyol powder are the same as described above for the DASC powder, with aluminum iso-propoxide and sodium bicarbonate being the preferred reactants. However, the reaction can be performed at a broader temperature of between about −20° C. and about 120° C. For the sake of ease, the reaction is preferably performed at room temperature. Suitable polyols again include but are not limited to sorbitol, glycerin, mannitol, maltodextrin, pentaerythritol, fructose, glucose and sucralose. However, hexitols such as sorbitol and mannitol are preferred.

The present invention also provides a stable, non-gritty suspension comprising either the DASC powder or the DASC/polyol powder of the present invention. The suspension may be prepared by admixing the powder with an aqueous solution at a w/w that results in the suspension having the desired physical properties. The inventors of the present invention have found that at a w/w of 1–15%, preferably at a w/w of 1–10%, and most preferably at a w/w of 2–6%, the suspension will be stable and non-gritty. However, it is within the confines of the present invention that higher or lower concentrations of the powder may be utilized if they result in a suspension having the desired properties.

The present inventors also have found that the suspensions of the present invention, depending upon the choice and concentration of polyol in the DASC/polyol powder, also possess other desirable properties in addition to stability and non-grittiness. For example, it has been found that the use of sorbitol, glycerin, mannitol, maltodextrin, pentaerythritol and fructose as the polyol can result in a suspension that not only is stable and non-gritty, but also is translucent. As used herein, "translucent" means that the suspension is not opaque such that light can pass through the suspension in a manner that permits the outline of objects (although not the details of such objects) to be seen through the suspension. In addition, it has been found that the use of polyols such as mannitol or fructose, for example, can result in a suspension that also has gelling properties.

Based upon the aforementioned properties, the powders or suspensions of the present invention are useful as components of various consumer or industrial products for which such properties are desirable. Such products include but are not limited to liquid antacids, tooth pastes, soaps, detergents, pharmaceuticals, lotions, nutriceuticals, plastic additives, chemical foaming agents, acid scavengers, gellants, cleaners, and the like. The formulation of such products with the powders and suspensions of the present invention are well within the purview of those skilled in the art.

However, because the suspensions are stable and non-gritty, and can be formulated to have an acceptable acid neutralizing capacity, the suspensions of the present invention are preferably used as the active ingredient in liquid antacid formulations. In this connection, it is preferred that the suspensions of the present invention have an acid neutralizing capacity (ANC) of 0.1–3.0, and more preferably an ANC of 0.5–1.0. However, higher or lower ANC values can be obtained if desired. The ANC can be determined using the procedures outlined in the U.S. Pharmacopoeia. In addition to the stability and non-gritty properties, the antacids can also be formulated to have gelling and/or translucent properties, as described above. In the particularly preferred embodiment, the liquid antacids are translucent, stable, non-gritty and non-gelling. Liquid antacids having these properties can be prepared as described in the examples below using polyols such as such sorbitol, glycerin, mannitol, maltodextrin, pentaerythritol and fructose. Finally, it is within the confines of the present invention that the liquid antacid formulations may be combined with flavoring agents, coloring agents, preservatives, and the like, if so desired.

The present invention is described in the following examples which are set forth to aid in the understanding of the invention, and should not be construed to limit in any way the invention as defined in the claims which follow thereafter.

EXAMPLE 1

Dry DASC And Water

A 5% (w/w) aqueous suspension of dry DASC, previously prepared essentially as described in Example 1 of U.S. Pat. No. 2,783,179, was stirred for about 30 minutes with gentle heating in order to ensure complete dispersion. The results are summarized in Table 1, and are as follows: ANC, not determined; Appearance, opaque; Stability, bad settling; Grittiness, bad; Evaluation, unacceptable.

EXAMPLE 2

DASC(Cold) Only/Salt Solution 97.9 g of sodium bicarbonate were added to 440 g of salt solution containing 40 g of sodium chloride and 400 g of ice, and cooled to −13° C. 204 g (1 mole) of aluminum isopropoxide were then added to the mixture and stirred for 1 hour. The resulting precipitate was isolated by vacuum filtration, air dried, and then oven dried at 100° C. overnight. A 5% (w/w) aqueous suspension of the material was then prepared, and stirred for about 30 minutes with gentle heating in order to ensure complete dispersion. The results are summarized in Table 1, and are as follows: ANC, 1.265; Appearance, semi-opaque; Stability, excellent; Grittiness, none; Evaluation, acceptable.

EXAMPLE 3

DASC(Cold) Only 146.9 g (1.75 moles) of sodium bicarbonate and 60 g isopropyl alcohol were added to 540 g of ice water, and cooled to −10° C. with dry ice. 306 g (1.5 moles) of aluminum iso-propoxide were then added to the mixture. The resulting precipitate was isolated by vacuum filtration, air dried, and then oven dried overnight. A 5% (w/w) aqueous suspension of the material was then prepared, and stirred for about 30 minutes with gentle heating in order to ensure complete dispersion. The results are summarized in Table 1, and are as follows: ANC, 1.065; Appearance, semi-opaque; Stability, excellent; Grittiness, none; Evaluation, acceptable.

EXAMPLE 4

Dry DASC(Room Temp.) And Sorbitol

Dry DASC, previously prepared essentially as described in Example 1 of U.S. Pat. No. 2,783,179, was reslurried with enough sorbitol to give a sorbitol/$Al_2O_3$ ratio of approximately 1:1. The slurry was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.920; Appearance, opaque; Stability, bad settling; Grittiness, bad; Evaluation, unacceptable.

EXAMPLE 5

DASC(Hot); Sorbitol Before Filtration 147 g (1.75 moles) of sodium bicarbonate were added to 540 g of water. 306 g (1.5 moles) of aluminum isopropoxide, heated to 100° C., then were added to the mixture and stirred for 1 hour. 128 g of a 70% sorbitol solution (90 g of 100% sorbitol and 38 g of water) then were added to the mixture, and stirred for 1 hour. The resulting precipitate was isolated by vacuum filtration, air dried, and then oven dried at 100° C. overnight. More than 50% of the sorbitol was lost in the filtration process. A 5% (w/w) aqueous suspension of the material then was prepared, and stirred for about 30 minutes with gentle heating in order to ensure complete dispersion. The results are summarized in Table 1, and are as follows: ANC, 0.947; Appearance, translucent; Stability, excellent; Grittiness, none; Evaluation, preferred.

EXAMPLE 6

Sodium Bicarbonate/Sorbitol/AIP(Hot)

147 g (1.75 moles) of sodium bicarbonate, 540 g of water, and 390 g of a 70% sorbitol solution (i.e. 273 g of 100% sorbitol and 170 g of water) were mixed. 306 g (1.5 moles) of aluminum iso-propoxide, heated to 100° C., then were added to the mixture and stirred for 2 hours. The resulting precipitate was isolated by vacuum filtration. Roughly half the batch filtered rather well. The filtered liquid and unfiltered solid were recombined to prevent loss of sorbitol, air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.677; Appearance, translucent; Stability, excellent; Grittiness, none; Evaluation, acceptable.

EXAMPLE 7

DASC(Cold); 70% Sorbitol After Filtration 146.9 g (1.75 moles) of sodium bicarbonate and 60 g isopropyl alcohol were added to 540 g of ice water, and cooled to −10° C. with dry ice. 306 g (1.5 moles) of aluminum iso-propoxide then were added to the mixture and stirred. The resulting precipitate was isolated by vacuum filtration and reslurried with 128 g of a 70% sorbitol solution (i.e. 90 g of 100% sorbitol and 38 g of water). After mixing, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.925; Appearance, translucent; Stability, excellent; Grittiness, none; Evaluation, preferred.

EXAMPLE 8

DASC(Room Temp); 70% Sorbitol After Filtration 147 g (1.75 moles) of sodium bicarbonate were added to 540 g of water at room temperature. 306 g (1.5 moles) of aluminum iso-propoxide then were added to the mixture and stirred. The resulting precipitate was isolated by vacuum filtration, and then reslurried with 128 g of a 70% sorbitol solution (i.e. 90 g of 100% sorbitol and 38 g of water). After mixing, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.910; Appearance, translucent; Stability, excellent; Grittiness, none; Evaluation, preferred.

EXAMPLE 9

DASC(Hot); 70% Sorbitol After Filtration 147 g (1.75 moles) of sodium bicarbonate were added to 540 g of water, and heated to 60–70° C. 306 g (1.5 moles) of aluminum iso-propoxide then were added to the mixture and stirred for 1 hour. The resulting precipitate was isolated by vacuum filtration, and then reslurried with 128 g of a 70% sorbitol solution (i.e. 90 g of 100% sorbitol and 38 g of water). After mixing, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, not determined; Appearance, translucent; Stability, excellent; Grittiness, none; Evaluation, acceptable.

EXAMPLE 10

DASC(Hot); 50% Sorbitol After Filtration 147 g (1.75 moles) of sodium bicarbonate were added to 540 g of water. 306 g (1.5 moles) of aluminum isopropoxide, heated to about 100° C., then were added to the mixture and stirred for 1 hour. The resulting precipitate was isolated by vacuum filtration, and then reslurried with 180 g of a 50% sorbitol solution (i.e. 90 g of 100% sorbitol and 90 g of water). After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.905; Appearance, translucent; Stability, excellent; Grittiness, none; Evaluation, preferred.

EXAMPLE 11

DASC(Hot); 30% Sorbitol After filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 300 g of a 30% sorbitol solution (i.e. 90 g of 100% sorbitol and 210 g of water). After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.990; Appearance, translucent; Stability, excellent; Grittiness, none; Evaluation, preferred.

EXAMPLE 12

DASC(Hot): 10% Sorbitol After Filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 51 g of a 70% sorbitol solution (i.e. 36 g of 100% sorbitol and 15 g of water). After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 1.159; Appearance, translucent; Stability, excellent; Grittiness, none; Evaluation, preferred.

EXAMPLE 13

DASC(Hot); 5% Sorbitol After Filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 26 g of a 70% sorbitol solution (i.e. 18 g of 100% sorbitol and 8 g of water). After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 1.109; Appearance, semi-translucent; Stability, excellent; Grittiness, minor; Evaluation, acceptable.

EXAMPLE 14

DASC(Hot); Glycerin After Filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 90 g of glycerin and enough water to form a homogeneous slurry. After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.926; Appearance, semi-translucent; Stability, excellent; Grittiness, none; Evaluation, acceptable.

EXAMPLE 15

DASC(Room Temp.); 50% Glycerin After Filtration 295.6 g (3.53 moles) of sodium bicarbonate were added to 2400 g of water. 629 g (3.1 moles) of aluminum isopropoxide then were added to the mixture and stirred for 1 hour at room temperature. The resulting precipitate was isolated by vacuum filtration. 50% of the filter cake then was added to a mixture of 46 g of glycerin dissolved in 700 g of water. After stirring for 10 minutes, the resulting mixture was fan dried, and then oven dried at 105–110° C. overnight. A 5% (w/w) aqueous suspension of the material then was prepared, and stirred for about 30 minutes with gentle heating in order to ensure complete dispersion. The results are summarized in Table 1, and are as follows: ANC, 1.158; Appearance, opaque; Stability, excellent; Grittiness, none; Evaluation, unacceptable for liquid antacids (acceptable for gelled antacids).

EXAMPLE 16

DASC(Hot); Mannitol After Filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 90 g of mannitol dissolved in 495 g of water. After mixing for 1 hour, the resulting mixture was air dried, and then oven dried at 100° C. overnight. A 5% (w/w) aqueous suspension of the material then was prepared, and stirred for about 30 minutes with gently heating in order to ensure complete dispersion. The results are summarized in Table 1, and are as follows: ANC, 1.150; Appearance, translucent; Stability, excellent; Grittiness, none; Evaluation, preferred.

EXAMPLE 17

DASC(Room Temp.): 50% Mannitol After Filtration 287.6 g (3.42 moles) of sodium bicarbonate were added to 2400 g of water. 612 g (3.0 moles) of aluminum isopropoxide then were added to the mixture and stirred for 1 hour at room temperature. The resulting precipitate was isolated by vacuum filtration. 50% of the filter cake was then added to a mixture of 44.8 g of mannitol dissolved in 1000 g of water. After stirring for 10 minutes, the resulting mixture was fan dried, and then oven dried at 105–110° C.

overnight. A 5% (w/w) aqueous suspension of the material then was prepared, and stirred for about 30 minutes with gentle heating in order to ensure complete dispersion. The results are summarized in Table 1, and are as follows: ANC, 1.067; Appearance, semi-translucent; Stability, excellent; Grittiness, minor; Evaluation, unacceptable for liquid antacids (acceptable for gelled antacids).

EXAMPLE 18

DASC(Room Temp.); Inositol After Filtration 287.6 g (3.42 moles) of sodium bicarbonate were added to 2400 g of water. 612 g (3.0 moles) of aluminum isopropoxide then were added to the mixture and stirred for 1 hour at room temperature. The resulting precipitate was isolated by vacuum filtration. 50% of the filter cake was then added to a mixture of 89.6 g of inositol dissolved in 900 g of water. After stirring for 10 minutes, the resulting mixture was fan dried, and then oven dried at 105°–110° C. overnight. A 5% (w/w) aqueous suspension of the material then was prepared, and stirred for about 30 minutes with gentle heating in order to ensure complete dispersion. The results are summarized in Table 1, and are as follows: ANC, 0.809; Appearance, semi-opaque; Stability, some settling; Grittiness, bad; Evaluation, unacceptable.

EXAMPLE 19

DASC(Room Temp.); 50% Inositol After Filtration 287.6 g (3.42 moles) of sodium bicarbonate were added to 2400 g of water. 612 g (3.0 moles) of aluminum isopropoxide then were added to the mixture and stirred for 1 hour at room temperature. The resulting precipitate was isolated by vacuum filtration. 50% of the filter cake was then added to a mixture of 44.8 g of inositol dissolved in 700 g of water. After stirring for 10 minutes, the resulting mixture was fan dried, and then oven dried at 105°–110° C. overnight. A 5% (w/w) aqueous suspension of the material then was prepared, and stirred for about 30 minutes with gentle heating in order to ensure complete dispersion. The results are summarized in Table 1, and are as follows: ANC, 1.025; Appearance, opaque; Stability, separated; Grittiness, none; Evaluation, unacceptable.

EXAMPLE 20

DASC(Hot); Pentaerythritol After Filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 90 g of pentaerythritol dissolved in 270 g of warm water. After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.885; Appearance, translucent; Stability, excellent; Grittiness, none; Evaluation, preferred.

EXAMPLE 21

DASC(Room Temp.); 50% Pentaerythritol After Filtration 287.6 g (3.42 moles) of sodium bicarbonate were added to 2400 g of water. 615 g (3.0 moles) of aluminum isopropoxide then were added to the mixture and stirred for 1 hour at room temperature. The resulting precipitate was isolated by vacuum filtration. 50% of the filter cake was then added to a mixture of 44.8 g of pentaerythritol dissolved in 700 g of water. After stirring for 10 minutes, the resulting mixture was fan dried, and then oven dried at 105°110° C. overnight. A 5% (w/w) aqueous suspension of the material then was prepared, and stirred for about 30 minutes with gentle heating in order to ensure complete dispersion. The results are summarized in Table 1, and are as follows: ANC, 1.077; Appearance, translucent; Stability, separated; Grittiness, none; Evaluation, unacceptable.

EXAMPLE 22

DASC(Hot); Sucrose After Filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 90 g of sucrose dissolved in 38 g of water. After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.945; Appearance, semi-opaque; Stability, bad settling; Grittiness, bad; Evaluation, unacceptable.

EXAMPLE 23

DASC(Hot); Maltodextrin After Filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 90 g of maltodextrin dissolved in 38 g of water. After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.885; Appearance, translucent; Stability, excellent; Grittiness, none; Evaluation, preferred.

EXAMPLE 24

DASC(Room Temp.); Acacia After Filtration 287.6 g (3.42 moles) of sodium bicarbonate were added to 2400 g of water. 612 g (3.0 moles) of aluminum isopropoxide then were added to the mixture and stirred for 1 hour at room temperature. The resulting precipitate was isolated by vacuum filtration. 50% of the filter cake was then added to a mixture of 89.6 g of acacia dissolved in 900 g of water. After stirring for 10 minutes, the resulting mixture was fan dried, and then oven dried at 105–110° C. overnight. A 5% (w/w) aqueous suspension of the material then was prepared, and stirred for about 30 minutes with gentle heating in order to ensure complete dispersion. The results are summarized in Table 1, and are as follows: ANC, 0.853; Appearance, opaque; Stability, bad settling; Grittiness, bad; Evaluation, unacceptable.

EXAMPLE 25

DASC(Room Temp.); Fructose After Filtration 287.6 g (3.42 moles) of sodium bicarbonate were added to 2400 g of water. 617 g (3.0 moles) of aluminum isopropoxide then were added to the mixture and stirred for 1 hour at room temperature. The resulting precipitate was isolated by vacuum filtration. 50% of the filter cake was then added to a mixture of 89.6 g of fructose dissolved in 700 g of water. After stirring for 10 minutes, the resulting mixture was fan dried, and then oven dried at 105–110° C. overnight. A 5% (w/w) aqueous suspension of the material then was prepared, and stirred for about 30 minutes with gentle heating in order to ensure complete dispersion. The results are summarized in Table 1, and are as follows: ANC, 0.920; Appearance, translucent; Stability, excellent; Grittiness, none; Evaluation, preferred.

EXAMPLE 26

DASC(Hot); Propylene Glycol After Filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 90 g of propylene glycol and enough water to form a homogeneous slurry. After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.970; Appearance, semi-opaque; Stability, minor settling; Grittiness, bad; Evaluation, unacceptable.

EXAMPLE 27

DASC(Hot); 1,3-Butylene Glycol After Filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 90 g of 1,3-butylene glycol and enough water to form a homogeneous slurry. After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 0.992; Appearance, opaque; Stability, bad settling; Grittiness, bad; Evaluation, unacceptable.

EXAMPLE 28

DASC(Hot); Neopentyl Glycol After Filtration 147 g (1.75 moles) of sodium bicarbonate were added to 540 g of water. 306 g (1.5 moles) of aluminum isopropoxide, heated to 100° C., then were added to the mixture and stirred for 1 hour. The resulting precipitate was isolated by vacuum filtration, and then reslurried with 90 g of neopentyl glycol dissolved in 38 g of water. After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, 1.005; Appearance, opaque; Stability, bad settling; Grittiness, bad; Evaluation, unacceptable.

EXAMPLE 29

DASC(Room Temp.); PEG (200 MW) After Filtration 287.6 g (3.42 moles) of sodium bicarbonate were added to 2400 g of water. 612 g (3.0 moles) of aluminum isopropoxide then were added to the mixture and stirred for 1 hour at room temperature. The resulting precipitate was isolated by vacuum filtration. 50% of the filter cake then was added to a mixture of 89.6 g of polyethylene glycol (200 MW) dissolved in 700 g of water. After stirring for 10 minutes, the resulting mixture was fan dried, and then oven dried at 105–110° C. overnight. A 5% (w/w) aqueous suspension of the material then was prepared, and stirred for about 30 minutes with gentle heating in order to ensure complete dispersion. The results are summarized in Table 1, and are as follows: ANC, 0.820; Appearance, opaque; Stability, separated; Grittiness, bad; Evaluation, unacceptable.

EXAMPLE 30

DASC(Room Temp.); PEG (1500 MW) After Filtration 287.6 g (3.42 moles) of sodium bicarbonate were added to 2400 g of water. 612 g (3.0 moles) of aluminum isopropoxide then were added to the mixture and stirred for 1 hour at room temperature. The resulting precipitate was isolated by vacuum filtration. 50% of the filter cake was then added to a mixture of 89.6 g of polyethylene glycol (1500 MW) dissolved in 700 g of water. After stirring for 10 minutes, the resulting mixture was fan dried, and then oven dried at 105–110° C. overnight. A 5% (w/w) aqueous suspension of the material then was prepared, and stirred for about 30 minutes with gentle heating in order to ensure complete dispersion. The results are summarized in Table 1, and are as follows: ANC, 0.869; Appearance, opaque; Stability, bad settling; Grittiness, bad; Evaluation, unacceptable.

EXAMPLE 31

DASC(Hot); Sodium Carboxymethylcellulose After Filtration 49 g (0.58 moles) of sodium bicarbonate were added to 180 g of water. 102 g (0.50 moles) of aluminum isopropoxide, heated to 100° C., then were added to the mixture and stirred for 1 hour. The resulting precipitate was isolated by vacuum filtration, and then reslurried with 30 g of sodium carboxymethylcellulose dispersed in 200 g of water. After mixing for 1 hour, the resulting mixture was air dried, and then oven dried at 100° C. overnight. A 5% (w/w) aqueous suspension of the material then was prepared, and stirred for about 30 minutes with gentle heating in order to ensure complete dispersion. The results are summarized in Table 1, and are as follows: ANC, not determined; Appearance, opaque; Stability, solidified; Grittiness, bad; Evaluation, unacceptable.

EXAMPLE 32

Replace AIP With ASB; Sorbitol After Filtration 143.7 g (1.7 moles) of sodium bicarbonate were added to 2000 g of water. 364.6 g (1.5 moles) of aluminum sec-butoxide then were added to the mixture and stirred for 1 hour at room temperature. The resulting precipitate was isolated by vacuum filtration. 50% of the filter cake was then added to 64 g of a 70% sorbitol solution (i.e. 45 g of 100% sorbitol and 19 g of water) dissolved in 350 g of water. After stirring for 10 minutes, the resulting mixture was fan dried, and then oven dried at 105°110° C. overnight. A 5% (w/w) aqueous suspension of the material then was prepared, and stirred for about 30 minutes with gentle heating in order to ensure complete dispersion. The results are summarized in Table 1, and are as follows: ANC, 0.964; Appearance, translucent; Stability, excellent; Grittiness, minor; Evaluation, acceptable.

TABLE 1

| Ex. | ANC | Appearance | Stability | Grit. | Evaluation* |
|---|---|---|---|---|---|
| 1 | N.D. | opaque | bad settl. | bad | unacceptable |
| 2 | 1.265 | semi-opaque | excellent | none | acceptable |
| 3 | 1.065 | semi-opaque | excellent | none | acceptable |
| 4 | 0.920 | opaque | bad settl. | bad | unacceptable |
| 5 | 0.947 | translucent | excellent | none | preferred |
| 6 | 0.677 | translucent | excellent | none | acceptable |
| 7 | 0.925 | translucent | excellent | none | preferred |
| 8 | 0.910 | translucent | excellent | none | preferred |
| 9 | N.D. | translucent | excellent | none | acceptable |
| 10 | 0.905 | translucent | excellent | none | preferred |
| 11 | 0.990 | translucent | excellent | none | preferred |
| 12 | 1.159 | translucent | excellent | none | preferred |
| 13 | 1.109 | translucent | excellent | minor | acceptable |
| 14 | 0.926 | semi-trans. | excellent | none | acceptable |
| 15 | 1.158 | opaque | excellent | none | unacceptable |
| 16 | 1.150 | translucent | excellent | none | preferred |
| 17 | 1.067 | semi-trans. | excellent | minor | unacceptable |
| 18 | 0.809 | semi-opaque | some settl. | bad | unacceptable |
| 19 | 1.025 | opaque | separated | none | unacceptable |
| 20 | 0.885 | translucent | excellent | none | preferred |
| 21 | 1.077 | translucent | separated | none | unacceptable |
| 22 | 0.945 | semi-opaque | bad settl. | bad | unacceptable |
| 23 | 0.885 | translucent | excellent | none | preferred |
| 24 | 0.853 | opaque | bad settl. | bad | unacceptable |
| 25 | 0.920 | translucent | excellent | none | preferred |
| 26 | 0.970 | semi-opaque | minor settl. | bad | unacceptable |
| 27 | 0.992 | opaque | bad settl. | bad | unacceptable |
| 28 | 1.005 | opaque | bad settl. | bad | unacceptable |
| 29 | 0.820 | opaque | separated | bad | unacceptable |
| 30 | 0.869 | opaque | bad settl. | bad | unacceptable |
| 31 | N.D. | opaque | solidified | bad | unacceptable |
| 32 | 0.964 | translucent | excellent | minor | acceptable |

*Evaluation based upon preferred suspensions for use in liquid antacid formulations. The preferred criteria were met by those suspensions having an ANC>0.8 (mEq of acid consumed per gram of suspension tested, as determined using Method 301 of USP23), translucent appearance, excellent stability and no grittiness. Examples 15 and 17, although unacceptable for liquid antacids, are acceptable for gelled antacids.

All issued U.S. patents mentioned hereinabove are hereby incorporated by reference in their entirety.

While the foregoing invention has been described in some detail for purposes of clarity and understanding, it will be appreciated by one skilled in the art from a reading of the disclosure that various changes in form and detail can be made without departing from the true scope of the invention in the appended claims.

What is claimed:

1. A process for preparing a dihydroxy aluminum sodium carbonate (DASC)/polyol powder comprising the steps of: (i) synthesizing DASC; (ii) isolating the synthesized DASC to provide isolated, undried DASC; (iii) mixing the isolated, undried DASC with water and at least one polyol selected from the group consisting of sorbitol, glycerin, mannitol, maltodextrin and fructose to form an aqueous DASC/polyol suspension; and (iv) drying the aqueous DASC/polyol suspension to form a DASC/polyol powder.

2. The process of claim 1, wherein DASC is synthesized by reacting an organoaluminum compound with a carbonate in an aqueous solution.

3. The process of claim 2, wherein the molar ratio of organoaluminum compound:carbonate is 1:1 to 1:3.

4. The process of claim 2, wherein the organoaluminum compound and the carbonate are reacted at a temperature of −20° C. to 120° C.

5. The process of claim 2, wherein the organoaluminum compound and the carbonate are reacted at room temperature.

6. The process of claim 2, wherein the organoaluminum compound is an aluminum alkoxide.

7. The process of claim 6, wherein the aluminum alkoxide is aluminum iso-propoxide, aluminum ethoxide or aluminum sec-butoxide.

8. The process of claim 7, wherein the aluminum alkoxide is aluminum iso-propoxide.

9. The process of claim 2, wherein the carbonate is sodium bicarbonate or sodium carbonate.

10. The process of claim 9, wherein the carbonate is sodium bicarbonate.

11. The process of claim 2, wherein the organoaluminum compound is aluminum iso-propoxide and the carbonate is sodium bicarbonate.

12. The process of claim 1, wherein the synthesized DASC is isolated by filtration, centrifugation, settling, decanting or a combination thereof.

13. The process of claim 1, wherein the isolated, undried DASC is washed with water before being mixed with the aqueous polyol.

14. The process of claim 1, wherein the weight ratio of DASC:polyol in step (iii) is 0.67:1 to 19:1.

15. The process of claim 1, wherein the weight ratio of DASC:polyol in step (iii) is 1.5:1 to 5:1.

16. The process of claim 1, wherein the polyol is sorbitol.

17. The process of claim 1, wherein the aqueous DASC/polyol suspension is dried by air-drying, oven-drying, fan-drying, spray-drying, or a combination thereof.

* * * * *